US009759671B2

(12) United States Patent
Grubert

(10) Patent No.: US 9,759,671 B2
(45) Date of Patent: Sep. 12, 2017

(54) DEVICE AND METHOD FOR MEASURING PANES, IN PARTICULAR WINDSCREENS OF VEHICLES

(71) Applicant: Möller-Wedel Optical GmbH, Wedel (DE)

(72) Inventor: Bernd Grubert, Wedel (DE)

(73) Assignee: Moller-Wedel Optical GmbH, Wedel (DE)

( * ) Notice: Subject to any disclaimer, the term of this patent is extended or adjusted under 35 U.S.C. 154(b) by 0 days.

(21) Appl. No.: 15/027,725

(22) PCT Filed: Sep. 25, 2014

(86) PCT No.: PCT/EP2014/070534
§ 371 (c)(1),
(2) Date: Apr. 7, 2016

(87) PCT Pub. No.: WO2015/052010
PCT Pub. Date: Apr. 16, 2015

(65) Prior Publication Data
US 2016/0238540 A1    Aug. 18, 2016

(30) Foreign Application Priority Data
Oct. 7, 2013   (DE) .................... 20 2013 008 910 U

(51) Int. Cl.
*G01N 21/00* (2006.01)
*G01N 21/958* (2006.01)
*G01B 11/26* (2006.01)

(52) U.S. Cl.
CPC ........... *G01N 21/958* (2013.01); *G01B 11/26* (2013.01); *G01N 2021/9586* (2013.01)

(58) Field of Classification Search
CPC ....... G01N 21/00; G01N 21/958; G01B 11/26
USPC ....................................... 356/239.1
See application file for complete search history.

(56) References Cited

U.S. PATENT DOCUMENTS

| 3,792,930 A * | 2/1974 | Obenreder ........... G01N 21/896 356/128 |
| 4,249,823 A | 2/1981 | Task |
| 4,837,449 A | 6/1989 | Maltby, Jr. |

(Continued)

OTHER PUBLICATIONS

International Search Report dated Dec. 17, 2014 (PCT/EP2014/070534).

*Primary Examiner* — Roy M Punnoose
(74) *Attorney, Agent, or Firm* — Alix, Yale & Ristas, LLP

(57) ABSTRACT

The invention relates to a device for measuring panes. The device comprises a light source and a light sensor which are arranged in such a way that a light beam emitted from the light source passes through the pane and impinges on the light sensor. According to the invention, the light beam has a linear polarization, wherein the polarization direction forms an angle of between 50° and 130° with an incidence plane stretching between the axis of the light beam and the pane normal at the point at which the light beam impinges on the pane. The light sensor is dimensioned such that both a primary beam and a secondary beam of the light beam impinge on the light sensor. The invention also relates to a corresponding method. According to the invention, the second beam has an increased brightness, so that it is easier to measure both beams.

14 Claims, 3 Drawing Sheets

(56) References Cited

U.S. PATENT DOCUMENTS

| | | | | |
|---|---|---|---|---|
| 5,059,023 A | * | 10/1991 | Task | G01M 11/00 356/239.1 |
| 5,146,282 A | * | 9/1992 | Guering | G01N 21/958 348/131 |
| 5,187,541 A | | 2/1993 | Task | |
| 5,726,749 A | * | 3/1998 | Schave | G01N 21/958 356/239.1 |
| 2010/0232677 A1 | * | 9/2010 | Bartsch | G01N 21/958 382/141 |
| 2011/0189426 A1 | | 8/2011 | Durbin et al. | |
| 2014/0029005 A1 | | 1/2014 | Fiess et al. | |

* cited by examiner

DEVICE AND METHOD FOR MEASURING PANES, IN PARTICULAR WINDSCREENS OF VEHICLES

BACKGROUND

The invention relates to a device and a method for measuring panes, more particularly windshields of vehicles. The device comprises a light source and a light sensor, which are arranged in such a way that a light beam emanating from the light source passes through the pane and is incident on the light sensor.

If a light beam is incident on a pane under an angle of incidence which includes an angle unequal to 0° with the normal of the pane, there may be internal reflection within the pane, by means of which the light beam is split into a primary beam and a secondary beam. An observer peering onto the light source through the pane sees a double image of the light source. A double image arises, in particular, if the pane is wedge-shaped in the relevant region, i.e. if the two outer faces are not parallel to one another, or if the pane is curved at said location.

By way of example, in the case of windshields of vehicles, such double images are perceived as bothersome if the light of an approaching vehicle is visible in duplicate form in darkness. It is known to measure windshields in respect of the generation of double images. The double image angle, i.e. the angle included between the primary beam and the secondary beam, is of particular interest. To this end, a light beam is guided through the pane onto a light sensor and the size of the distance between the primary beam and the secondary beam on the light sensor is established.

In these measurements, the problem arises that it is not entirely straightforward to measure the primary beam and the secondary beam on a light sensor since the primary beam is regularly many times brighter than the secondary beam.

SUMMARY

The invention is based on the object of providing a device by means of which the double images generated by a pane can be measured more easily. The object is achieved by the features of claim 1. Advantageous embodiments are specified in the dependent claims.

According to the invention, the light beam has a linear polarization, wherein the polarization direction includes an angle of between 50° and 130° with the plane of incidence. The plane of incidence is spanned by the axis of the light beam incident on the pane and the normal of the pane at the location at which the light beam is incident on the pane.

At first, a few terms are explained. A light beam can be described as a superposition of a multiplicity of electromagnetic waves, wherein each individual wave has a linear polarization direction that is directed perpendicular to the direction of propagation of the light. The light beam formed by the superposition of the individual waves has a linear polarization if the individual waves of the relevant polarization direction are present in the light beam with a higher intensity than other polarization directions. It would be ideal for the invention if the light beam were to be composed exclusively from individual waves of the relevant linear polarization direction. In practice, this will usually not be realizable, and it will be necessary to make do with the relevant polarization direction being present with a significantly higher intensity than other polarization directions. The pane is transparent such that the light beam can pass therethrough. The pane preferably consists of a material, the refractive index of which is greater than the refractive index of air. The pane is not a component of the device according to the invention.

The invention proposes, when measuring the pane, for the linear polarization of the light beam to be aligned in a targeted manner relative to the plane of incidence of the light beam. The plane of incidence is spanned by the axis of the light beam and the normal of the pane at the location at which the light beam is incident on the pane. The normal of the pane denotes the axis that is at right angles to an imaginary tangential plane placed onto the pane at the location at which the light beam is incident. The light source should be arranged in such a way that the light beam does not coincide with the normal of the pane.

According to the invention, the polarization direction of the light beam encloses an angle of between 50° and 130° with the plane of incidence. If the light beam impinges on the pane with such a polarization direction, the brightness of the secondary beam increases and it becomes easier to measure the primary beam and the secondary beam. The light sensor is dimensioned such that both the primary beam and the secondary beam of the light beam impinge on the light sensor.

The difference in the brightness between the primary beam and the secondary beam is caused by the fact that the primary beam crosses the pane directly while the secondary beam experiences two additional reflections in the interior of the pane. The magnitude of the portion of the reflected light compared to the portion of the transmitted light depends, inter alia, on the polarization direction of the light. In accordance with the invention, the polarization direction of the light is selected in such a way that an increased portion of the light is reflected in the interior of the pane, i.e. contributes to the brightness of the secondary beam. The greatest brightness of the secondary beam is achieved when the polarization direction of the light beam includes an angle of 90° with the plane of incidence. Then, the brightness of the secondary beam is higher by a factor of approximately 2 than in the case of a non-polarized light beam. A relevant increase in the brightness sets in in an angular range between 50° and 130°. Preferably, the angle lies between 70° and 110°, more preferably between 80° and 100°.

After the emergence from the pane, the primary beam and the secondary beam are spatially separated from one another in such a way that they can be evaluated separately from one another by means of the light sensor. Depending on the wedge angle and the curvature of the pane, the primary beam and the secondary beam include an angle therebetween, as a consequence of which the distance between the two beams increases with the distance from the pane.

The light sensor can have an evaluation unit which automatically establishes the position of the primary beam and of the secondary beam on the light sensor. Such an evaluation unit renders it possible to automate the measurement of the pane overall. It is possible to calculate specific properties of the pane in an automatic manner, for example whether the pane meets certain standards. Appropriate information can be output on a display of the evaluation unit.

For the measurement, it is advantageous to use a concentrated light beam, the extent of which across the direction of propagation is small. If the light beam is collimated, the measurement result is independent of the distance between the light source and the pane. By way of example, a collimated light beam can be obtained by virtue of arranging a suitable collimation lens between the light source and the pane. In a preferred embodiment, a laser is used as a light source, said laser emitting a collimated light beam per se.

The linear polarization can be obtained by the light beam by virtue of said light beam passing through a suitable polarization filter between the light source and the pane. The polarization filter is transmissive to light with the relevant polarization direction, while other polarization directions are damped or preferably completely suppressed. Additionally or alternatively, use can be made of a light source; by way of example, the use of a He—Ne laser with a suitable linear polarization comes into question.

The alignment of the plane of incidence can depend on the position at which the light beam is incident on the pane. In order to be able to adapt the direction of polarization to different planes of incidence, it is advantageous if the polarization filter and/or the light source is/are designed in such a way that the linear polarization direction is adjustable. Preferably, the relevant element is mounted in a manner rotatable about the axis of the light beam.

If the primary beam and the secondary beam include an angle therebetween, the distance between the two beams is dependent on the distance at which the pane is measured. Consequently, an exact adjustment of the distance between the pane and the light sensor is generally required in order to be able to draw conclusions about the properties of the pane from the positions of the primary beam and the secondary beam on the light sensor.

In an advantageous embodiment, a converging lens through which the primary beam and the secondary beam pass is arranged between the pane and the light sensor. If the light sensor is arranged in the focal plane of the converging lens, the position of primary beam and secondary beam on the light sensor is independent of the distance between the pane and the converging lens. The device can be configured in such a way that the light sensor and the converging lens are components of an analysis instrument, in which the light sensor and the converging lens are held at a fixed distance from one another. Measuring the pane is made easier in this way because the light sensor has the appropriate distance from the converging lens and the distance between the converging lens and the pane does not influence the measurement. Consequently, the relevant adjustment is dispensed with.

It is not necessary for the converging lens according to the invention to be an individual lens element. Rather, the same effect can be achieved if the converging lens is a lens system made of a plurality of individual lens elements and the light sensor is arranged in the focal plane of the lens system. The diameter of the converging lens is preferably greater than 30 mm and can, for example, lie between 40 mm and 60 mm. With these dimensions, the converging lens is regularly suitable for capturing both the primary beam and the secondary beam.

Even if the polarization direction of the light beam is set according to the invention, the primary beam is still brighter by a multiple than the secondary beam. The brightness of the primary beam can be higher, for example, by a factor of 30, than the brightness of the secondary beam. Typical light sensors ascertain the brightness of the incident beam with a dynamic range of 8 bit at linear resolution. It is possible to distinguish thus between 256 brightness stages. The brightness stages are linear, which means that the brightness difference between 2 neighbouring brightness stages is substantially identical over the entire bandwidth.

It is difficult with such a light sensor to measure the primary beam and the secondary beam at the same time, because the brightness difference between the 2 beams substantially covers the entire dynamic range of the light sensor. If the sensitivity of the light sensor is set such that the primary beam corresponds to the uppermost brightness stages, the secondary beam is practically lost in the noise. If the sensitivity is increased such that the secondary beam can be measured definitively, the light sensor is overdriven by the primary beam.

For this reason, it is possible within the context of the invention to use a light sensor, the dynamic range of which is greater than 8 bit with linear resolution. In an advantageous embodiment, the dynamic range corresponds to at least 12 bit in the case of a linear resolution. A light sensor with a nonlinear resolution can contribute to increasing the dynamic range. Preferably, the nonlinear resolution is selected in such a way that the brightness distance between two adjacent brightness levels increases with increasing brightness. In a preferred embodiment, the light sensor has a logarithmic resolution. The fact that a light sensor with a logarithmic resolution is generally less suitable for distinguishing between closely adjacent brightness levels is not a relevant disadvantage within the scope of the invention because only two light beams, the brightness levels of which differ significantly, are to be detected.

The light sensor preferably has a sensor face covered by a multiplicity of pixels. The resolution according to the invention is preferably provided for the individual pixels.

The invention moreover relates to a method for measuring panes. In the method, a light beam is guided through a pane onto a light sensor. According to the invention, the light beam has a linear polarization. The polarization direction encloses an angle of between 50° and 130° with the plane of incidence. The plane of incidence is defined by the axis of the light beam and the pane normal at the location at which the light beam impinges on the pane. The method can be developed with further features which are described in the context of the device according to the invention.

BRIEF DESCRIPTION OF THE DRAWINGS

The invention is described in an exemplary manner below on the basis of an advantageous embodiment, with reference being made to the attached drawings. In detail.

DETAILED DESCRIPTION

Figure 1:
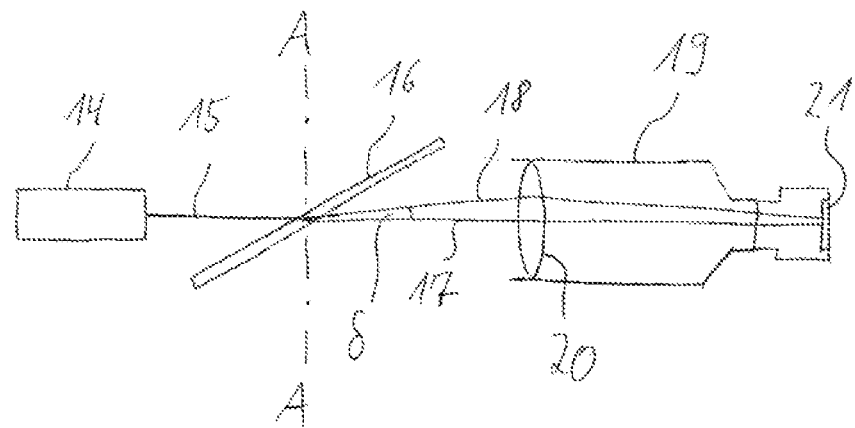
FIG. 1 shows a schematic illustration of a device according to the invention.

A device according to the invention in FIG. 1 comprises a light source 14 in the form of a He—Ne laser. The light source 14 emits a collimated light beam 15 in the direction of a windshield 16 of a motor vehicle to be measured. The light beam 15 is incident on the pane 16 at an acute angle. When passing through the pane 16, the light beam is split into a primary beam 17 and a secondary beam 18 which, when leaving the pane 16, include a double image angle δ therebetween.

The primary beam 17 and the secondary beam 18 are captured by an analysis instrument 19. The analysis instrument 19 comprises a tube-shaped housing, at the front end of which a converging lens 20 is arranged. The converging lens 20 forms an objective of the analysis instrument 19, through which the primary beam 17 and secondary beam 18 enter into the housing. Arranged at the other end of the housing is a light sensor 21, on which the primary beam 17 and the secondary beam 18 are incident. By way of example, the light sensor 21 can be a CCD camera. The distance between the converging lens 20 and the light sensor 21 corresponds to the focal length of the converging lens 20; i.e., the light sensor 21 is arranged in the focal plane of the converging lens 20. By way of example, the converging lens 20 can have a diameter of 50 mm and a focal length of 300 mm.

The primary beam 17 and the secondary beam 18 are incident on the light sensor 21 with a distance d therebetween. Since the light sensor 21 is arranged in the focal plane of the converging lens 20, the distance d is not dependent on the distance between the converging lens 20 and the pane 16. It is therefore not necessary to bring the analysis instrument 19 to an exactly defined distance from the pane 16. The double image angle δ can be established from the distance d according to the following formula:

$$\delta = \arctan \frac{d}{f} \approx \frac{d}{f}$$

Here, f denotes the focal length of the converging lens 20. For small angles (less than 0.1 radians), the double image angle δ emerges as approximately the quotient of d and f. From the double image angle δ, it is possible to draw conclusions about the properties of the pane 16, for example about geometric properties in the region in which the light beam 15 passed through the pane 16.

Figure 2:
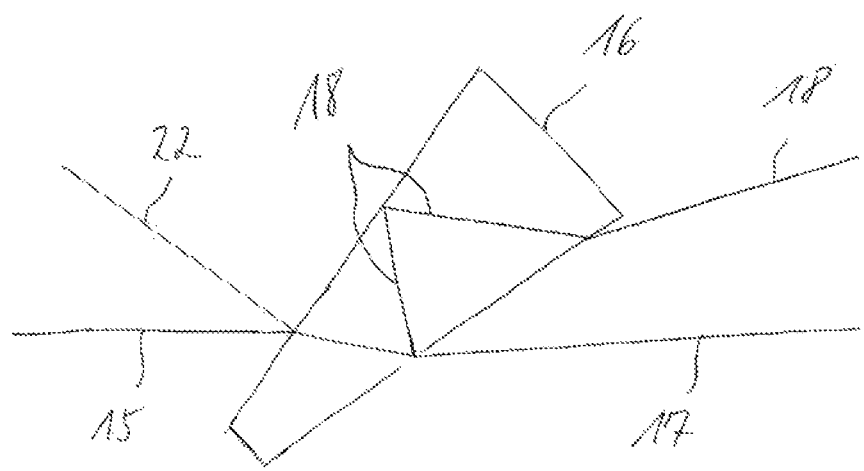
FIG. 2 shows a magnified section from FIG. 1 in the case of a pane with a wedge angle.
Figure 3:
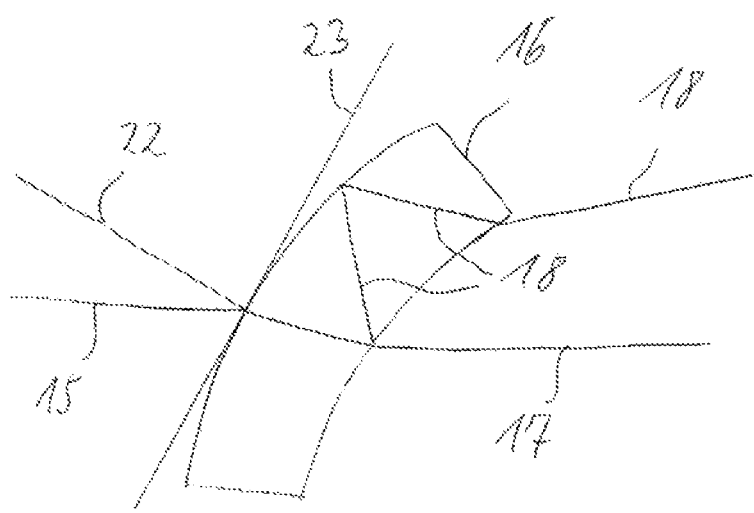
FIG. 3 shows a magnified section from FIG. 1 in the case of a pane with a curve.

In accordance with FIG. 2, the splitting of the light beam 15 into the primary beam 17 and the secondary beam 18 emerges, for example, during the passage of the light beam 15 through a pane 16 which has a wedge angle, i.e. in which the two outer faces are not parallel to one another. In accordance with FIG. 3, a corresponding split into the primary beam 17 and secondary beam 18 emerges when the light beam 15 passes through a curved pane 16. By way of example, it is possible to draw conclusions about the wedge angle or the radius of curvature of the pane 16 from the double image angle δ. Moreover, by way of a comparison with corresponding thresholds, it is possible to determine whether the double image angle δ itself meets the specifications.

The light beam 15 coming from the light source 14 spans the plane of incidence with the normal 22 of the pane. The normal 22 of the pane is perpendicular to the pane 16 at the location at which the light beam 15 is incident on the pane 16. In the case of a curved pane 16, the normal 22 of the pane is perpendicular to the tangential plane 23 which is placed against the pane 16 at the relevant location, see FIG. 3.

Figure 4:
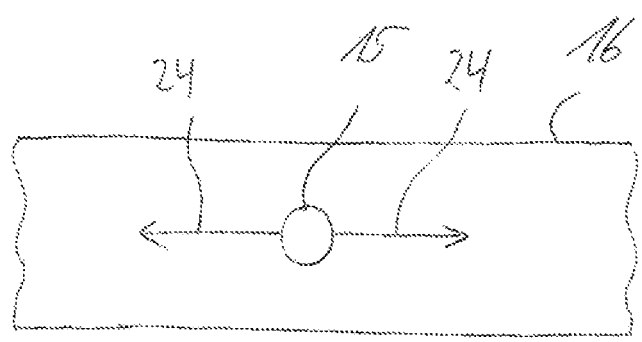
FIG. 4 shows a magnified sectional illustration along the line A-A in FIG. 1.

The light beam 15 generated by the light source 14 is collimated and has a linear polarization. The polarization direction 24, which is indicated by two arrows in FIG. 4, is aligned perpendicular to the plane of incidence 15, 22. Compared to a non-polarized light beam, the brightness of the secondary beam 18 is increased by approximately a factor of 2 as a result of the selection of the polarization direction.

The light sensor 21 is a matrix sensor which has a matrix made of light-sensitive photodiodes. In each photodiode, the incidence of a light beam releases a number of charge carriers, said number being proportional to the brightness. A brightness level is established on the basis of the number of charge carriers and an assignment between the photodiode and the brightness level is undertaken. In the case of a conventional linear assignment, the number of charge carriers increases linearly from brightness level to brightness level, as a consequence of which the dynamic range of the light sensor 21 is restricted.

An increased dynamic range is desired for the device according to the invention, which is why the light sensor 21 has a logarithmic resolution. The number of released charge carriers therefore increases exponentially from brightness level to brightness level. As a result, the light sensor 21 has an increased dynamic range and it is possible to establish both the primary beam 17 and the secondary beam 18 sufficiently accurately with the light sensor 21, even if the primary beam 17 is, for example, brighter than the secondary beam 18 by a factor of 30.

Figure 5:
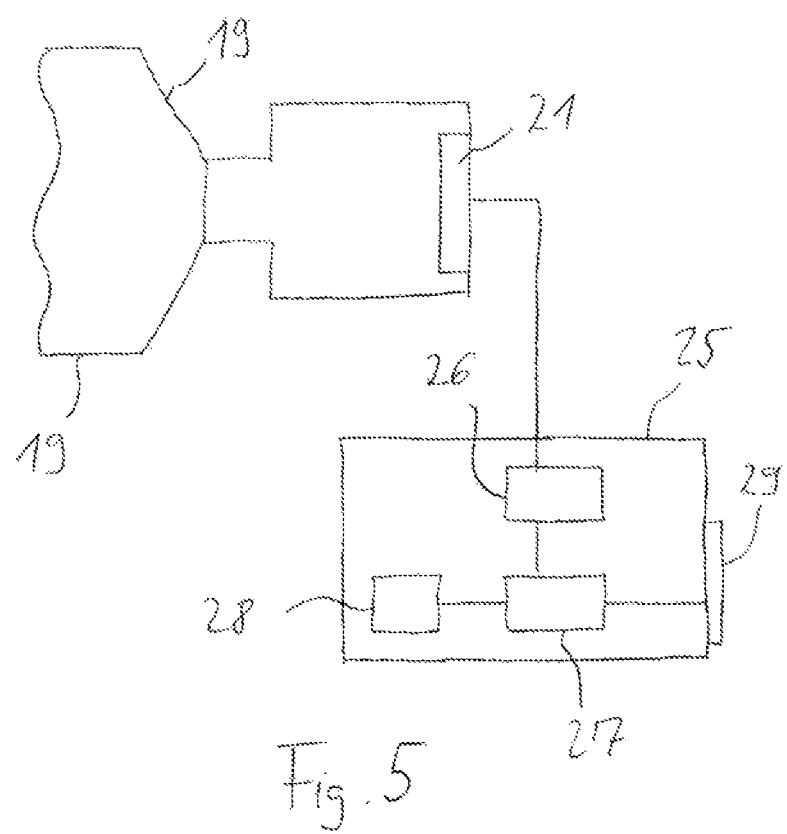
FIG. 5 shows a block diagram of an evaluation unit according to the invention.

In accordance with FIG. 5, the digital values are guided from the light sensor 21 to an evaluation unit 25 and stored in a memory 26 there. A computational module 27 establishes the distance d with which the primary beam 17 and the secondary beam 18 are incident on the light sensor 21 from the values stored in the memory 26. On the basis of the known focal length f of the converging lens 20, the double image angle δ which the primary beam 17 and the secondary beam 18 include when emerging from the pane 16 can be established in a further computational step. A setpoint value for the double image angle δ is stored in a second memory 28. The computational module 27 compares the established value with the value from the memory 28 and outputs information on a display 29 as to whether the pane 16 meets the specifications.

The invention claimed is:

1. A device for measuring double images generated by a pane, comprising a light source and a light sensor, which are arranged in such a way that a light beam emanating from the light source passes through a pane and is incident on the light sensor, wherein the light beam has a linear polarization and in that a polarization direction of the light beam includes an angle of between 50° and 130° with a plane of incidence, which is defined by an axis of the light beam and a normal of the pane at a location at which the light beam impinges on the pane, and in that the light sensor is dimensioned in such a way that both a primary beam and a secondary beam of the light beam are incident on the light sensor.

2. The device as claimed in claim 1, wherein the polarization direction includes an angle with the plane of incidence which is between 70° and 110°.

3. The device as claimed in claim 1, wherein the light sensor has an evaluation unit which establishes the position of the primary beam and the secondary beam on the light sensor in an automatic manner.

4. The device as claimed in claim 1, wherein the light beam is collimated.

5. The device as claimed in claim 1, wherein the light source is a laser.

6. The device as claimed in claim 1, wherein the linear polarization direction is adjustable.

7. The device as claimed in claim 1, wherein a converging lens through which the light beam passes is arranged between the pane and the light sensor.

8. The device as claimed in claim 7, wherein the light sensor is arranged in a focal plane of the converging lens.

9. The device as claimed in claim 1, wherein a dynamic range of the light sensor is greater than 8 bit.

10. The device as claimed in claim 9, wherein the dynamic range of the light sensor is at least 12 bit.

11. The device as claimed in claim 9, wherein the light sensor has a nonlinear resolution such that a brightness distance between two adjacent brightness levels increases with increasing brightness.

12. The device as claimed in claim 9, wherein the light sensor has a logarithmic resolution.

13. A method for measuring double images generated by a pane comprising the following steps:
 a. guiding a linearly polarized light beam through a pane onto a light sensor such that a polarization direction of the light beam encloses an angle of between 50° and 130° with a plane of incidence, wherein the plane of incidence is defined by an axis of the light beam and a normal of the pane at a location at which the light beam impinges on the pane;
 b. ascertaining a position of a primary beam on the light sensor;
 c. ascertaining a position of a secondary beam on the light sensor.

14. The device as claimed in claim 1, wherein the polarization direction includes an angle with the plane of incidence which is preferably between 80° and 100°.

* * * * *